US008211430B2

(12) United States Patent
Levetan et al.

(10) Patent No.: US 8,211,430 B2
(45) Date of Patent: *Jul. 3, 2012

(54) METHODS AND PHARMACEUTICAL COMPOSITIONS FOR TREATING TYPE 1 DIABETES MELLITUS AND OTHER CONDITIONS

(75) Inventors: Claresa S. Levetan, Bryn Mawr, PA (US); Loraine V. Upham, Albuquerque, NM (US)

(73) Assignee: Curedm Group Holdings, LLC, Wilmington, DE (US)

( * ) Notice: Subject to any disclaimer, the term of this patent is extended or adjusted under 35 U.S.C. 154(b) by 249 days.

This patent is subject to a terminal disclaimer.

(21) Appl. No.: 11/367,682

(22) Filed: Mar. 3, 2006

(65) Prior Publication Data

US 2006/0198839 A1 Sep. 7, 2006

Related U.S. Application Data

(60) Provisional application No. 60/658,965, filed on Mar. 4, 2005, provisional application No. 60/682,087, filed on May 18, 2005, provisional application No. 60/684,819, filed on May 25, 2005.

(51) Int. Cl.
*A61K 39/00* (2006.01)
*A61K 39/38* (2006.01)

(52) U.S. Cl. .................................. 424/133.1; 424/184.1
(58) Field of Classification Search .......................... None
See application file for complete search history.

(56) References Cited

U.S. PATENT DOCUMENTS

| 4,444,887 A | 4/1984 | Hoffmann |
|---|---|---|
| 4,716,111 A | 12/1987 | Osband et al. |
| 4,757,060 A | 7/1988 | Lukacsko et al. |
| 4,816,397 A | 3/1989 | Boss et al. |
| 4,816,567 A | 3/1989 | Cabilly et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,436,169 A | 7/1995 | Iovanna et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,580,859 A | 12/1996 | Felgner et al. |
| 5,585,089 A | 12/1996 | Queen et al. |
| 5,631,224 A | 5/1997 | Efendic et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,766,886 A | 6/1998 | Studnicka et al. |
| 5,780,225 A | 7/1998 | Wigler et al. |
| 5,807,715 A | 9/1998 | Morrison et al. |
| 5,821,047 A | 10/1998 | Garrard et al. |
| 5,834,590 A | 11/1998 | Vinik et al. |
| 5,840,531 A | 11/1998 | Vinik et al. |
| 5,959,086 A | 9/1999 | Iovanna et al. |
| 5,969,108 A | 10/1999 | McCafferty |
| 6,311,415 B1 | 11/2001 | Lind |
| 6,407,213 B1 | 6/2002 | Carter et al. |
| 6,645,934 B1 | 11/2003 | Rodemann et al. |
| 6,946,151 B2 | 9/2005 | Chatterji |
| RE39,062 E | 4/2006 | Vinik et al. |
| RE39,299 E | 9/2006 | Vinik et al. |
| 7,166,439 B2 | 1/2007 | Vinik et al. |
| 7,393,919 B2 | 7/2008 | Levetan et al. |
| 7,714,103 B2 | 5/2010 | Levetan et al. |
| 7,989,415 B2 | 8/2011 | Levetan et al. |
| 2003/0035803 A1* | 2/2003 | McMichael ............... 424/146.1 |
| 2003/0212000 A1* | 11/2003 | Van Antwerp .................. 514/12 |
| 2004/0132644 A1 | 7/2004 | Vinik et al. |
| 2005/0084449 A1 | 4/2005 | Landes et al. |
| 2005/0249806 A1 | 11/2005 | Proehl et al. |
| 2007/0087971 A1 | 4/2007 | Levetan et al. |
| 2007/0184504 A1 | 8/2007 | Vinik et al. |
| 2008/0300190 A1 | 12/2008 | Levetan et al. |
| 2009/0068145 A1 | 3/2009 | Levetan et al. |
| 2009/0142338 A1 | 6/2009 | Levetan |
| 2010/0093605 A1 | 4/2010 | Levetan et al. |
| 2011/0171178 A1 | 7/2011 | Levetan et al. |

FOREIGN PATENT DOCUMENTS

| EP | 0303233 A2 | 2/1989 |
|---|---|---|
| EP | 239400 | 8/1994 |
| EP | 1329458 A | 12/2000 |
| EP | 592106 | 11/2004 |
| EP | 519596 | 2/2005 |
| WO | WO 90/02809 | 3/1990 |
| WO | WO 91/09967 | 7/1991 |
| WO | WO 91/10737 | 7/1991 |
| WO | WO 91/10741 | 7/1991 |
| WO | WO 92/01047 | 1/1992 |
| WO | WO 92/18619 | 10/1992 |
| WO | WO 92/22324 | 12/1992 |

(Continued)

OTHER PUBLICATIONS

Rosenberg, L., et al. Ann. Surg. 2004;240(5):875-884.*
Tam, J., et al. FASEB J. 2004;18(4):1-23.*
Casteels, K.M., et al. Endocrionology. 1998;139(1):95-102.*
Rabinovitch, A., et al. Diabetes. 2002;51:638-645.*
Biron et al., A Monomeric 310-Helix is Formed in Water by a 13-Residue Peptide Representing the Neutralizing Determinant of HIV-1 on gp41, Biochemistry (2002) 41(42):12687-12696.
Buse, et al., Amylin replacement with pramlinlide in type 1 and type 2 diabetes: A physiological approach to overcome barriers with insulin therapy, Clin. Diab. (2002) 20:137-144.
Levetan, et al., Reduced Postprandial Glucose, Glueagon and Triglyceride Excursions Following 4 Weeks of Pramlintide Treatment in Patients with Type 1 Diabetes Treated Intensively with Insulin Pumps, Abstracts from 62nd Ann. Meeting in San Francisco, CA, Diabetes (Jun. 2002) 51(Suppl. 2):474-P:A117 (Abstract).

(Continued)

*Primary Examiner* — Gerald R Ewoldt
(74) *Attorney, Agent, or Firm* — Pepper Hamilton LLP

(57) ABSTRACT

Methods for treating type 1 diabetes mellitus or a condition resulting from the loss of pancreatic islet cells in a patient are disclosed herewith. The method of treatment comprises co-administration of human proislet peptides (HIP); and an agent that inhibits the activity of autoimmune cells.

12 Claims, No Drawings

FOREIGN PATENT DOCUMENTS

| | | |
|---|---|---|
| WO | WO 93/11236 | 6/1993 |
| WO | WO 9317105 | 9/1993 |
| WO | WO 95/15982 | 6/1995 |
| WO | WO 95/20401 | 8/1995 |
| WO | WO 96/19236 A1 | 6/1996 |
| WO | WO 96/26215 A1 | 8/1996 |
| WO | WO 96/33735 | 10/1996 |
| WO | WO 96/34096 | 10/1996 |
| WO | WO 97/13844 | 4/1997 |
| WO | WO 98/16654 | 4/1998 |
| WO | WO 98/24893 | 6/1998 |
| WO | WO 98/46645 | 10/1998 |
| WO | WO 98/50433 | 11/1998 |
| WO | WO 03/033808 | 4/2003 |
| WO | WO 03/105897 A1 | 12/2003 |
| WO | WO 2006/128083 A2 | 11/2006 |

OTHER PUBLICATIONS

Ludvigsson et al., GAD Treatment and Insulin Secretion in Recent-Onset Type 1 Diabetes, N Engl J Med (Oct. 30, 2008) 359(18):1909-1920.

Mishra, et al., Studies of Synthetic Peptides of Human Apolipoprotein A-I Containing Tandem Amphipathic α-Helixes, Biochemistry (1998) 37(28):10313-10324.

Igarashi, et al. Role of GLP-1, Internal Secretion/Diabetes Department, Jan. 28, 2005, vol. 20, No. 1, p. 69-74.

Ronit et al., Closing and Sequencing of the Pancreatic Islet Neogenesis Associated Protein (INGAP) Gene and Its Expression in Islet Neogenesis in Hamsters, *J. CLin. Invest.* (May 1997) 99(9):2100-2109.

Yamaoka, Regeneration therapy for diabetes mellitus, *Expert Opin. Biol. Ther.* (2003) 3(3):425-433.

Want et al., Reduced Postprandial Glucose, Glucagon and Triglyceride Excursions Following 4 Weeks of Pramlintide Treatment in Patients with Type 1 Diabetes Treated Intensively with Insulin Pumps, 2002, Diabetes 51(suppl. 2):474-P.

Rosenberg et al., Trophic Stimulation of the Ductular-Islet Cell Axis: A New Approach to the Treatment of Diabetes, 1992, Adv. Exp. Med. Biol. 321:95-104.

Rosenberg et al., Islet-cell regeneration in the diabetic hamster pancreas with restoration of normoglycaemia can be induced by a local growth factor(s) Mar. 1996, Diabetologia 39(3):256-262.

Rosenberg et al., Induction of Islet Cell Differentiation and New Islet Formation in the Hamster-Further Support for a Ductular Origin, Jul. 1996, Pancreas 13(1):38-46.

Rosenberg et al., A Pentadecapeptide Fragment of Islet Neogenesis-Associated Protein Increases Beta-Cell Mass and Reverses Diabetes in C57BL/6J Mice, Nov. 2004, Ann. Surg. 240(5):875-884.

Vinik et al., Induction of Pancreatic Islet Neogenesis, Jun. 1997, Horm. Metab. Res. 29(6):278-293.

Young et al., Amylin's physiology and its role in diabetes, 1997, Curr. Opin. Endocrin. Diabetes 4(4):282-290.

Marquez et al., Inositolphosphoglycans Possibly Mediate the effects of Glucagon-Like Peptide-1(7-36)amide on Rat Liver and Adipose Tissue, 1998, Cell Biochem. Funct. 16(1):51-56.

Dupre et al., Exendin-4 Normalized Postcibal Glycemic Excursions in Type 1 Diabetes, 2004, J. Clin. Endocrin. Metab. 89(7):3469-3473.

Edwards et al., Glucagon-Like Peptide 1 Has a Physiological Role in the Control of Postprandial Glucose in Humans, 1999, Diabetes 48:86-93.

Xu et al., Exendin-4 Stimulates Both β-Cell Replication and Neogenesis, Resulting in Increased β-Cell Mass and Improved Glucose Tolerance in Diabetic Rats, 1999, Diabetes 48:2270-2276.

Creutzfeldt, The Incretin Concept Today, 1979, Diabetologia 16:75-85.

Creutzfeldt et al., New developments in the incretin concept, 1985, Diabetologia 28:565-573.

Holst et al., Incretin hormones-an update, 2001, Scand. J. Clin. Lab. Invest. 61, Suppl. 234:75-85.

Vilsboll et al., Incretin Secretion in Relation to Meal Size and Body Weight in Healthy Subjects and People with Type 1 and Type 2 Diabetes Mellitus, Jun. 2003, J. Clin. Endocrin. Metab. 88(6):2706-2713.

Andersen et al., Oral Glucose Augmentation of Insulin Secretion, 1978, J. Clin. Invest. 62:152-161.

Creutzfeldt et al., Inhibition of Gastric Inhibitory Polypeptide (GIP) Release by Insulin and Glucose in Juvenile Diabetes, 1980, Diabetes 29(2):140-145.

Dupre et al., Stimulation of Insulin Secretion by Gastric Inhibitory Polypeptide, 1973, J. Clin. Endocrin. Metab. 37:826-828.

Ebert et al., Gastric Inhibitory Polypeptide, 1980, Clin. in Gastroenterology 9(3):679-698.

Elahi et al., Pancreatic α-and β-cell responses to GIP infusion in normal man, 1979, Am. J. Physiol. 237:E185-E191.

Elahi et al., The insulinotropic actions of glucose-dependent insulinotropic polypeptide (IP) and glucagon-like peptide-1 (7-37) in normal and diabetic subjects, 1994, Regulatory Peptide 51(1):63-74.

Krarup et al., Diminished Immumoreactive Gastric Inhibitory Polypeptide Response to a Meal in Newly Diagnosed Type 1 (Insulin-Dependent) Diabetics, Jun. 1983, J. Clin. Endocrin. Metab. 56(6):1306-1312.

Krarup et al., Gastric Inhibitory Polypeptide in Newly Diagnosed Ketotic Type 1 (Insulin-dependent) Diabetics, 1988, Acta Med. Scand. 223(5):437-441.

Lynn et al., A novel pathway for regulation of glucose-dependent insulinotropic polypeptide (GIP) receptor expression in β cells, 2003, FASEB 17:91-93.

Meir et al., Gastric Inhibitory Polypeptide: the neglected incretin revisited, 2002, Regulatory Peptides 107:1-13.

Nauck et al., Additive Insulinotropic Effects of Exogenous Synthetic Human Gastric Inhibitory Polypeptide and Glucagon-Like Peptide-1-(7-36) Amide Infused at Near-Physiological Insulinotropic Hormone and Glucose Concentrations, 1993, J. Clin. Endocrin. Metab. 76(4):912-917.

Jones et al., A supplementary infusion of glucose-dependent insulinotropic polypeptide (GIP) with a meal does not significantly improve the β cell response or glucose tolerance in type 2 diabetes mellitus, Nov. 6, 1989, Diabetes Res. Clin. Prect. 7(4):263-269.

Elahi et al., The insulinotropic actions of glucose-dependent insulinotropic polypeptide (GIP) and glucagon-like peptide-1 (7-37) in normal and diabetic subjects, 1994, Regulatory Peptides 51(1):63-74.

Gutniak et al., Subcutaneous Injection of the Incretin Hormone Glucagon-Like Peptide 1 Abolishes Postprandial Glycemia in NIDDM, 1994, Diabetes Care 17(9):1039-1044.

Kreymann et al., Glucagon-Like Peptide-1 7-36: A Physiological Incretin in Man, 1987, Lancet 2:1300-1304.

Larsen et al., One-Week Continuous Infusion of GLP-1(7-37) Improves the Glycaemic Control in NIDDM, 1996, Diabetes 45(Suppl. 2):233A (860) (Abstract).

Larsen et al., Glucagon-Like Peptide-1 Infusion Must be Maintained for 24h/day to Obtain Acceptable Glycemia in Type 2 Diabetic Patients Who Are Poorly Controlled on Sulphonylurea Treatment, 2001, Diabetes Care 24(8):1416-1421.

List et al., Glucagon-like peptide 1 agonists and the development and growth of pancreatic β-cells, 2004, Am. J. Physiol. Endocrin. Metab. 286(6): E875-E881.

Lugari et al., Effect of Nutrient Ingestion on Glucagon-Like Peptide 1 (7-36 Amide) Secretion in Human Type 1 and Type 2 Diabetes, 2000, Horm. Metab. Res. 32:424-428.

Marquez et al., Inositolphosphoglycans Possibly Mediate the Effects of Glucagon-Like Peptide-1 (7-36)amide on Rat Liver and Adipose Tissue, Mar. 1998, Cell. Biochem. Funct. 16(1):51-56.

Meier et al., Intravenous glucagon-like peptide 1 normalizes blood glucose after surgery inpatients with type 2 diabetes, Mar. 2004, Critical Care Medicine 32(3):848-851.

Meneilly et al., Effects of 3 Months of Continuous Subcutaneous Administration of Glucagon-Like Peptide 1 in Elderly Patients with Type 2 Diabetes, 2003, Diabetes Care 26(10):2835-2841.

Nauck et al., Effects of subcutaneous glucagon-like peptide 1 (GLP-1 [7-36]) in patients with NIDDM, 1996, Diabetologia 39(12):1546-1553.

Thorens et al., Glucagon-Like Peptide-1 and Control of Insulin Secretion, Dec. 1995, Diabetes Metab. 21(5):311-318.

Vilsboll et al., Incretion Secretion in Relation to Meal Size and Body Weight in Healthy Subjects and People with Type 1 and Type 2 Diabetes Mellitus, 2003, J. Clin. Endocrin. Metab. 88(6):2706-2713.
Wang et al., Glucagon-like peptide-1 Can Reverse the Age-related Decline in Glucose Tolerance in Rats, 1997, J. Clin. Invest. 99:2883-2889.
Zander et al., Effect of 6-week course of glucagon-like peptide 1 on glycaemic control, insulin sensitivity, and β-cell function in type 2 diabetes: a parallel-group study, 2002, Lancet 359:824-830.
Mathis et al., β-Cell death during progression to diabetes, Dec. 2001, Nature 414(6865):792-798.
Herold et al., Anti-CD3 Monoclonal Antibody in New-Onset Type 1 Diabetes Melitus, May 30, 2002, NEJM 346(22):1692-1698.
Raz et al., β-cell function in new-onset type 1 diabetes and immunomodulation with a heat-shock protein peptide (DiaPep277): a randomized, double-blind, phase II trial, 2001, Lancet, 358(9295):1749-1753.
Davis et al., The effects of HDV-insulin on carbohydrate metabolism in Type 1 diabetic patients, 2001, J. Diabetes Comp. 15(5):227-233.
Ogawa et al., Cure of Overt Diabetes in NOD Mice by Transient Treatment with Anti-Lymphocyte Serum and Exendin-4, 2004, Diabetes 53(7):1700-1705.
Rafaeloff et al., Cloning and Sequencing of the Pancreatic Islet Neogenesis Associated Protein (INGAP) Gene and Its Expression in Islet Neogenesis in Hamsters, J. Clin. Invest., May 1997, 99(9):2100-2109.
Jamal et al., Morphogenetic Plasticity of Adult Human Pancreatic Islets of Langerhans, Apr. 8, 2005, Cell Death Differ. 12:702-712.
Hopp et al., Prediction of protein antigenic determinants from amino acid sequences, 1981, Proc. Natl. Acad. Sci. USA 78(6):3824-3828.
Hammerling et al., Monoclonal Antibodies and T-Cell Hybridomas, Perspectives and technical advances. Elsevier, NY, 1981 (TOC).
Brinkmann et al., Phage display of disulfide-stabilized Fv fragments, 1995, J. Immunol. Methods 182:41-50.
Ames et al., Conversion of murine Fabs isolated from a combinatorial phage display library to full length immunoglobulins, 1995, J. Immunol. Methods 184:177-186.
Kettleborough et al., Isolation of tumor cell-specific single-chain Fv from immunized mice using phage-antibody libraries and the reconstruction of whole antibodies from these antibody fragments, 1994, Eur. J. Immunol. 24:952-958.
Persic et al., An integrated vector system for the eukaryotic expression of antibodies or their fragments after selection from phage display libraries, 1997, Gene 187:9-18.
Burton et al., Human Antibodies from Combinatorial Libraries, 1994, Advances in Immunology 57:191-280.
Mullinax et al., Expression of a Heterodimeric Fab Antibody Protein in One Cloning Step, 1992, BioTechniques 12(6):864-869.
Sawai et al., Direct Production of the Fab Fragment Derived from the Sperm Immobilizing Antibody Using Polymerase Chain Reaction and cDNA Expression Vectors, 1995, AJRI 34:26-34.
Better et al., *Escherichia coli* Secretion of an Active Chimeric Antibody Fragment, 1988, Science 240:1041-1043.
Morrison, Transfectomas Provide Novel Chimeric Antibodies, 1985, Science 229:1202-1207.
Oi et al., Chimeric Antibodies, 1986, BioTechniques 4(3):214.
Gillies et al., High-level expression of chimeric antibodies using adapted cDNA variable region cassettes, 1989, J. Immunol. Methods 125:191-202.
Padlan, A Possible Procedure for Reducing the Immunogenicity of Antibody Variable Domains While Preserving Their Ligand-Binding Properties, 1991, Molecular Immunology 28(4/5):489-498.
Studnicka et al., Human-engineered monoclonal antibodies retain full specific binding activity by preserving non-CDR complementarity-modulating residues, 1994, Protein Engineering 7(6):805-814.
Roguska et al., Humanization of murine monoclonal antibodies through variable domain resurfacing, 1994, PNAS 91:969-973.
Tan et al., "Superhumanized" Antibodies: Reduction of Immunogenic Potential by Complementarity-Determining Region Grafting with Human Germline Sequences: Application to an Anti-CD28, 2002, J. Immunol. 169:1119-1125.
Caldas et al., Design and synthesis of germline-based hemi-humanized single-chain Fv against the CD18 surface antigen, 2000, Protein Eng. 13(5):353-360.
Morea et al., Antibody Modeling: Implications for Engineering and Design, 2000, Methods 20(3):267-279.
Baca et al., Antibody Humanization Using Monovalent Phage Display, 1997, J. Biol. Chem. 272(16):10678-10684.
Roguska et al., A Comparison of two murine monoclonal antibodies humanized by CDR-grafting and variable domain resurfacing, 1996, 9(10):895-904.
Couto et al., Designing Human Consensus Antibodies with Minimal Positional Templates, 1995, Cancer Res. 55 (23 Suppl):5973s-5977s.
Couto et al., Anti-BA46 Monoclonal Antibody Mc3: Humanization Using a Novel Positional Consensus and in Vivo and in Vitro Characterization, 1995, Cancer Res. 55(8):1717-1722.
Sandhu, A rapid procedure for the humanization of monoclonal antibodies, 1994, Gene 150(2):409-410.
Pederson et al., Comparison of Surface Accessible Residues in Human and Murine Immunoglobulin Fv Domains, 1994, J. Mol. Biol. 235(3):959-973.
Riechmann et al., Reshaping human antibodies for therapy, 1988, Nature 332:323:327.
Wu et al., Adapters, Linkers and Methylation, 1987, Methods in Enzymol. 152:343-349.
Foecking et al., Powerful and versatile enhancer-promoter unit for mammalian expression vectors, 1986, Gene 45:101-105.
Cockett et al., High Level Expression of Tissue Inhibitor of Metalloproteinases in Chinese Hamster Ovary Cells Using Glutamine Synthetase Gene Amplification, 1990, Bio/Technology 8:662-667.
Inouye & Inouye, Up-promoter mutations in the *Ipp* gene of *Escherichia coli*, 1985, Nucleic Acids Res. 13(9):3101-3109.
Logan et al., Adenovirus tripartite leader sequence enhances translation of mRNAs late after infection, 1984, Proc. Natl. Acad. Sci. USA8 81:3655-3659.
Wu et al., Delivery systems for gene therapy, 1991, Biotherapy 3:87-95.
Tolstoshev, Gene Therapy, Concepts, Current Trials and Future Directions, 1993, Ann. Rev. Pharmacol. Toxicol. 32:573-596.
Mulligan, The Basic Science of Gene Therapy, 1993, Science 260:926-932.
Morgan et al., Human Gene Therapy, 1993, Ann. Rev. Biochem. 62:191-217.
Wigler et al., Transformation of mammalian cells with an amplifiable dominant-acting gene, 1980, Natl. Acad. Sci. USA 77(6):3567-3570.
Ohare et al., Transformation of mouse fibroblasts to methotrexate resistance by a recombinant plasmid expressing a prokaryotic dihydrofolate reductase, 1981, Proc. Natl. Acad. Sci. USA 78(3):1527-1531.
Mulligan et al., Selection for animal cells that express the *Escherichin coli* gene coding for xanthine-guanine phosphoribosyltransferase, 1981, Proc. Natl. Acad. Sci. USA 78(4):2072-2076.
Santerre et al., Expression of prokaryotic genes for hygromycin B and G418 resistance as dominant-selection markers in mouse L cells, 1984, Gene 30:147-156.
Colbere-Garapin et al., A New Dominant Hybrid Selective Marker for Higher Eukaryotic Cells, 1981, J. Mol. Biol. 150:1-14.
Merrifield, Solid Phase Peptide Synthesis, The Synthesis of a Tetrapeptide, 1963, J. Am. Chem. Soc. 85:2149-2154.
Delovitch et al., The Nonobese Diabetic Mouse as a Model of Autoimmune Diabetes: Immune Dysregulation Gets the NON, 1997, Immunity 7:727-738.
Van Heeke et al., Expression of Human Asparagine Synthetase in *Escherichia coli*, 1989, J. Biol. Chem. 264(10):5503-5509.
Lewis et al., Improved glucose control in nonhospitalized pregnant diabetic patients, 1976, Obstet. Gynecol. 48(3):260-267.
Ilic et al., Is the paradoxical first trimester drop in insulin requirement due to an increase in C-peptide concentration in pregnant Type I diabetic women? 2000, Diabetologia 43:1329-1330.
Jovanovic et al., Declining Insulin Requirement in the Late First Trimester of Diabetic Pregnancy, 2001, Diabetes Care 24:1130-1136.
Holick et al., Prevalence of Vitamin D Inadequacy among Postmenopausal North American Women Receiving Osteoporosis Therapy, 2005, J. Clin. Endocrinol. Metab. 90:3215-3224.

Riachy et al., 1,25-dihydroxyvitamin $D_3$ protects human pancreatic islets against cytokine-induced apoptosis via down-regulation of the fas receptor, Feb. 2006, Apoptosis 11(2):151-159.

Holick, High Prevalence of Vitamin D Inadequacy and Implications for Health, Mar. 2006, Mayo Clin. Proc. 81(3):353-373.

Grant, Epidemiology of disease risks in relation to vitamin D insufficiency, Feb. 28, 2006, Prog. Biophys. Mol. Biol. 92:65-79.

Dicesar et al., Vitamin D Deficiency is More Common in Type 2 Than in Type 1 Diabetes, Jan. 2006, Diabetes Care, 29(1):174.

Reis et al., Vitamin D endocrine system and the genetic susceptibility to diabetes, obesity and vascular disease, A review of evidence, 2005, Diabetes Metab. 31:318-325.

Pozzilli et al., Low Levels of 25-hydroxyvitamin $D_3$ and 1,25-dihydroxyvitamin $D_3$ in Patients with Newly Diagnosed Type 1 Diabetes, 2005, Horm. Metab. Res. 37(11):680-683.

Vieth et al., Efficacy and safety of vitamin $D_3$ intake exceeding the lowest observed adverse effect level [1-3], 2001, Am. J. Clin. Nutr. 73:288-294.

Yoon et al., Selective β-Cell Loss and α-Cell Expansion in Patients with Type 2 Diabetes Mellitus in Korea, 2003, J. Clin. Endocrinol. Metab. 88(5):2300-2308.

Li et al., Islet loss and alpha cell expansion in type 1 diabetes induced by multiple low-dose streptozotocin administration in mice, 2000, J. Endocrinol. 165:93-99.

Vukkadapu et al., Dynamic interaction between T cell-mediated β-cell damage and β-cell repair in the run up to autoimmune diabetes of the NOD mouse, Apr. 14, 2005, Physiol. Genomics, 21(2):201-211.

Hao et al., Beta-cell differentiation from nonendocrine epithelial cells of the adult human pancreas, 2006, Nature Medicine 12(3):310-316.

Jamal et al., Morphogenetic plasticity of adult human pancreatic islets of Langerhans, Jul. 2005, Cell Death Differ. 12(7):702-712.

Herold et al., A Single Course of Anti-CD3 Monoclonal Antibody hOKT3γ1 (Ala-Ala) Results in Improvement in C-Peptide Responses and Clinical Parameters for at Least 2 Years after Onset of Type 1 Diabetes, 2005, Diabetes 54(6):1763-1769.

Agardh et al., Clinical evidence for the safety of GAD65 immunomodulation in adult-onset autoimmune diabetes, 2005, J. Diabetes Complications, 19(4):238-246.

Krarup et al., Effect of Porcine Gastric Inhibitory Polypeptide on β-cell Function in Type I and Type II Diabetes Mellitus, 1987, Metabolism 36(7):677-682.

Bonner-Weir et al., The pancreatic ductal epithelium serves as a potential pool of progenitor cells, 2004, Pediatric Diabetes 5(Suppl 2):16-22.

Bitter et al., Expression and Secretion Vectors for Yeast, 1987, Methods in Enzymol. 153:516-544.

\* cited by examiner

SEQUENCE LISTING

<160> NUMBER OF SEQ ID NOS: 8

<210> SEQ ID NO 1
<211> LENGTH: 14
<212> TYPE: PRT
<213> ORGANISM: Homo sapiens

<400> SEQUENCE: 1

Ile Gly Leu His Asp Pro Thr Gln Gly Thr Glu Pro Asn Gly
1               5                   10

<210> SEQ ID NO 2
<211> LENGTH: 15
<212> TYPE: PRT
<213> ORGANISM: Homo sapiens

<400> SEQUENCE: 2

Ile Gly Leu His Asp Pro Thr Gln Gly Thr Glu Pro Asn Gly Glu
1               5                   10                  15

<210> SEQ ID NO 3
<211> LENGTH: 17
<212> TYPE: PRT
<213> ORGANISM: Homo sapiens

<400> SEQUENCE: 3

Val Trp Ile Gly Leu His Asp Pro Thr Gln Gly Thr Glu Pro Asn Gly
1               5                   10                  15

Glu

<210> SEQ ID NO 4
<211> LENGTH: 6
<212> TYPE: PRT
<213> ORGANISM: Homo sapiens

<400> SEQUENCE: 4

Ile Gly Leu His Asp Pro
1               5

<210> SEQ ID NO 5
<211> LENGTH: 7
<212> TYPE: PRT
<213> ORGANISM: Homo sapiens

<400> SEQUENCE: 5

Trp Ile Gly Leu His Asp Pro
1               5

<210> SEQ ID NO 6
<211> LENGTH: 15
<212> TYPE: PRT
<213> ORGANISM: Homo sapiens

<400> SEQUENCE: 6

Trp Ile Gly Leu His Asp Pro Thr Gln Gly Thr Glu Pro Asn Gly
1               5                   10                  15

<210> SEQ ID NO 7
<211> LENGTH: 16
<212> TYPE: PRT
<213> ORGANISM: Homo sapiens

<400> SEQUENCE: 7

```
Trp Ile Gly Leu His Asp Pro Thr Gln Gly Thr Glu Pro Asn Gly Glu
1               5                   10                  15

<210> SEQ ID NO 8
<211> LENGTH: 7
<212> TYPE: PRT
<213> ORGANISM: Homo sapiens

<400> SEQUENCE: 8

Ile Gly Leu His Asp Pro Thr
1               5
```

METHODS AND PHARMACEUTICAL COMPOSITIONS FOR TREATING TYPE 1 DIABETES MELLITUS AND OTHER CONDITIONS

RELATED APPLICATIONS

This application claims priority to U.S. Ser. No. 60/658,965, filed Mar. 4, 2005, U.S. Ser. No. 60/682,087, filed May 18, 2005 and U.S. Ser. No. 60/684,819, filed May 25, 2005, each of which are incorporated herein by reference in their entireties.

FIELD OF THE INVENTION

The present invention provides methods and pharmaceutical compositions for treating type 1 diabetes mellitus and other conditions and so relates to the fields of biochemistry, pharmacology, and medicine.

BACKGROUND

Since 1922, insulin has been the only available therapy for the treatment of type diabetes and other conditions related to lack of or diminished production of insulin. Despite decades of research and the advent of pancreatic islet cell transplantation in 1974 and newer claims of success resulting from the Edmonton Protocol for islet cell transplantation, the success has not been replicated in the United States. At four years post-transplant, fewer than 10% of patients who have received islet cell transplants remain insulin independent. Additionally, despite new immune suppression protocols, there is an 18% rate per patient of serious side effects.

Over the past several decades, there have been several newly identified peptide sequences involved in glucose metabolism, some of which are believed to be the most potent islet stimulating hormones. These hormones include peptide sequences of Glucagon Like Peptide-1 (GLP-1) and its analogs, Gastric Inhibitory Peptide/Glucose-Dependent Insulinoptropic polypeptide (GIP), Amylin, and its analog, Pramlintide, and homologous compounds to GLP-1, such as Liraglutide (NN2211) and Exendin-4, Islet Neogenesis Associated Peptide (INGAP), the biologically active hamster INGAP peptides, other nonhuman mammalian INGAP analogs, the Human proIslet Peptide and biologically active peptides having significant homology to the Human ProIslet Peptide, and biologically active derivatives of the Human proIslet Peptide and hamster INGAP peptide, which derivatives can include amino acid additions and/or substitutions in the Human proIslet Peptide and hamster INGAP peptide, and/or compounds that block the degradation of Human proIslet Peptide, hamster INGAP, GLP-1, GLP-1 receptor analog, such as Exendin-4 or Liraglutide, or GLP-1 analogs, or compounds which halt the destruction of GLP-1, such as Dipeptidyl Peptidase-4 Inhibitors, which may have the potential to regenerate pancreatic islet cells that produce insulin and other stimulators of islet regeneration and include but are not limited to Vilidagliptin, Sidagliptin, Saxagliptin and PHX1149. Other agents which also have the potential to expand islet cell mass include gastrin and epidermal growth factor-1. Proof of the elasticity of the pancreas with respect to the generation of new pancreatic cells throughout one's lifetime accompanied by pancreatic cell death or apoptosis has replaced the long held concept that the number of insulin producing islet cells is fixed at birth and sustained throughout life. It is currently well accepted that pancreatic islet cell neogenesis occurs from preexisting islet cells and through transformation from exocrine ductal cells. Data demonstrates that, even decades after the onset of 1 diabetes, insulin producing islet cells can be regenerated. For example, patients with type 1 diabetes who can make normal levels of c-peptide during pregnancy and patients who have been on long term immunosuppression for kidney transplantation have been observed to regenerate insulin producing islet cells.

Additionally, over the past decade, clinical trials have been conducted to evaluate the impact of a number of immune modulators that may arrest the destruction of the pancreas. The studies and types of agents to potentially arrest the destruction of islet cells have varied considerably. The types of agents include general immunosuppressant agents which have typically been used in organ transplants, specifically targeted antibodies to those lympocytes which attack the islets, along with other agents such as Vitamin D, in which a deficiency has been associated with an higher incidence of diabetes.

Anti CD-3 antibodies that target the immune response and specifically block the T-lymphocytes that cause islet cell death in type 1 diabetes have been utilized as well as heat-shock proteins to arrest the destruction of insulin-producing cells and anti-GAD65 antibody vaccines. Trials are underway with a number of diverse agents or combination of agents among newly diagnosed patients with diabetes. Currently the immune agents Mycophenolate mofetil and Daclizumab, which have been used to suppress rejection among organ transplants patients is being studied for usage in newly diagnosed type 1 diabetes patients. Rituximab, an anti CD20 agent, which is an FDA approved agent for the treatment of B-lymphocyte lymphoma, is also being studied in the preservation of islet cells among newly diagnosed diabetes patients. Early trials have shown promising results and ongoing trials are underway in newly type 1 diabetes patients using the anti CD3 antibody, hOKT3 gamma1 (Ala-Ala) and the monoclonal antibody TRX4 (ChAglyCD3).

DiaPep277 is another immune agent directed at the onset of type 1 diabetes to halt the destruction of islets. DiaPep277 is a heat shock protein 50 which is believed to impact the Th1 cells which release cytokines and pro-inflammatory cells which destroy islet cells, is being studied in adults and children with newly diagnosed patients with diabetes and also in patients with Latent Autoimmune Diabetes in Adults (LADA).

The aim of all of the therapies that are proposed to prevent further immune destruction of the islet cells, does not enhance further replication of new islet cells, which is a very slow process. Typically, a healthy individual requires about 1.5 million islet cells to maintain glucose homeostatsis. At the time of diagnosis, both type 1 and type 2 patients only retain about 50% of their typical islet cell mass. This ongoing destructive process in type 1 diabetes is typically more rapid and progressive than in type 2 diabetes leading to multiple daily insulin injections to survive. The typical healthy adult has a usual cell death rate for islets of between 1000 and 2000 cells per day; the human islet lifespan being about 3 years. Each day, the same number of new islets are formed from precursor cells within the pancreas, both in the endocrine and exocrine portions of the organ. Thus, even if immune-halting agents to prevent further islet loss, because the daily regeneration rate of new islet production is only about 0.1% per day, it could take years to repopulate the pancreas with insulin producing without such an immune-blocking compound being combined with a regeneration compound such as Human proIslet Peptide, a DPP-4 inhibitor, and GLP-1 agonist, or GLP-1 receptor agonist.

To date, however, there has been no single or combination therapy that has been successfully used to treat the underlying disease mechanisms of type 1 diabetes or conditions in which there is a lack of or diminished insulin production. There remains a need for new methods and pharmaceutical compositions for treating type 1 diabetes mellitus. Especially needed are methods and compositions that can also treat the many other conditions in which the lack of or diminished insulin production has a causative role or contributes to the symptoms of patients in need of treatment. At present, there appears to be no treatment that ameliorates the symptoms of type 1 diabetes by targeting the underlying disease mechanism. The present invention meets the need for improved therapies for treating type 1 diabetes and other conditions.

SUMMARY OF THE INVENTION

In a first aspect, the present invention provides a method for treating type 1 diabetes mellitus in a patient, said method comprising administering to said patient an agent that stimulates pancreatic islet cell regeneration and/or transformation of new insulin producing islet cells from pancreatic ductal epithelium in combination with an agent that is specifically designed to inhibit the activity of or kill or otherwise cause the death of autoimmune cells that can cause the death of the pancreatic islet cells that produce insulin. The method is particularly efficacious, because, unlike prior therapies, the therapeutic methods of the invention not only promote islet cell regeneration but also inhibit the autoimmune cells caused the destruction of the islet cells and therefore the insulin dependency of the patient.

In a second aspect, the present invention provides methods for one or more agents that stimulate pancreatic islet cell regeneration and/or transformation of new insulin producing islet cells from pancreatic ductal epithelium to treat diabetes and other diseases and conditions relating to aberrant glucose regulation. In various embodiments, these methods involved the administration of such agents, including but not limited to Human proIslet Peptide, hamster INGAP, exendin-4, including synthetic exendin-4, and Liraglutide (NN221), which are GLP-1 receptor analogs or other agents which increase plasma GLP-1 levels and may have the potential to regenerate pancreatic islet cells that produce insulin and other stimulators of islet regeneration and include but are not limited to Vilidagliptin, Sidagliptin, Saxagliptin and PHX1149. Other agents which also have the potential to expand islet cell mass include gastrin and epidermal growth factor-1. Theses agents may be used alone or in combination with each other. These methods can be practiced to treat a number of diabetes related conditions, including but not limited to type 1 diabetes, where these treatments can be used to improve glycemic control, as measured by hemoglobin A1C, and to reduce bolus insulin before meals by 10-20%, with reduced fluctuations and decreased postprandial glucose, glucagon, and triglycerides. These methods can also be used to prevent progression of impaired glucose tolerance to diabetes and to prevent progression of impaired fasting glucose to progression to impaired glucose tolerance and diabetes and to reverse newly diagnosed type 2 diabetes. These methods can also be used to treat type 2 diabetes.

In a third aspect, the present invention provides compositions useful in the methods of the invention.

DETAILED DESCRIPTION OF THE INVENTION

To aid in understanding the invention, the detailed description of the invention is organized as follows. Section I provides helpful definitions. Section II provides detailed information regarding the methods of the invention and the agents and compositions useful therein. Section II is further subdivided into subsections, with subsection A providing an overview of the method; subsection B providing information regarding type 1 diabetes mellitus and other conditions that can be treated with the methods and compositions of the invention; subsection C providing information regarding agents useful in stimulating pancreatic islet cell regeneration; and subsection D providing information regarding agents that inhibit the activity of or destroy or otherwise cause the death of autoimmune cells that target pancreatic islet cells. Section III describes pharmaceutical formulations provided by or useful in the methods of the invention as well as dosing and administration protocols that constitute important methods of the invention.

I. Definitions

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of diabetes, diminishment of extent of disease, delay or slowing of disease progression, amelioration, palliation or stabilization of the disease state, and other beneficial results described below.

As used herein, "reduction" of a symptom or symptoms (and grammatical equivalents of this phrase) means decreasing of the severity or frequency of the symptom(s), or elimination of the symptom(s).

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "manifestation" of a disease refers to a symptom, sign, anatomical state (e.g., lack of islet cells), physiological state (e.g., glucose level), or report (e.g., triglyceride level) characteristic of a subject with the disease.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a prophylactically effective amount may be administered in one or more administrations.

As used herein, "TID", "QD" and "QHS" have their ordinary meanings of "three times a day", "once daily," and "once before bedtime", respectively.

Administration of an agent "in combination with" includes parallel administration (administration of both the agents to the patient over a period of time, such as administration of a monoclonal antibody and a peptide hormone such as an incretin hormone or analog on alternate days for one month), co-administration (in which the agents are administered at approximately the same time, e.g., within about a few minutes to a few hours of one another), and co-formulation (in which the agents are combined or compounded into a single dosage form suitable for oral or parenteral administration).

DPP-4 is dipeptidyl peptidase-4 inhibitor.

HIP (or PIP) is a human proIslet Peptide. PIP and analogs and derivatives thereof of the invention include the polypeptides shown below in Table 2.

Table 2. Sequence of Human Proislet Peptide (PIP) and Analogs

TABLE 2

Sequence of Human Proislet Peptide (PIP) and analogs

| | | |
|---|---|---|
| IGLHDPTQGTEPNGE | PIP | SEQ ID NO: 2 |
| IGLHDPTQGTEPNG | Glutamate-less PIP | SEQ ID NO: 1 |
| VWIGLHDPTQGTEPNGE | Valine-Tryp PIP Analog | SEQ ID NO: 3 |
| IGLHDP | Hexapeptide PIP | SEQ ID NO: 4 |
| WIGLHDP | Septapeptide PIP | SEQ ID NO: 5 |
| WIGLHDPTQGTEPNG | Tryp-Glutamate-less PIP | SEQ ID NO: 6 |
| WIGLHDPTQGTEPNGE | Tryp-PIP | SEQ ID NO: 7 |
| IGLHDPT | Second Septapeptide PIP | SEQ ID NO: 8 |

INGAP is islet neogenesis associated peptide derived from the Hamster

GIP is Gastric Inhibitory Peptide, also known as Glucose-Dependent Insulinotropic Polypeptide.

GLP-1 is Glucagon-like Peptide 1.

II. Methods of the Invention and Agents Useful Therein

A. Overview of the Methods of the Invention

The present invention provides combination therapies and methods for treating type 1 diabetes mellitus and related conditions in which there is a lack of or diminished insulin production in a patient by administering to that patient an agent that stimulates pancreatic islet cell regeneration and/or transformation from pancreatic ductal cells into islet cells and the simultaneous or contemporaneous administration of an agent that inhibits the activity of and or blocks or destroys the autoimmune cells that target pancreatic islet cells. Prior to the present invention, there has been no prior use of the diverse therapeutic regimens to provide the unique combination of both an islet regeneration and/or transformation agent with targeted immunomodulation to prevent islet cell death in patients with type 1 diabetes and other conditions in which there is inadequate or diminished insulin levels. The new therapeutic methods provided by the present invention address several different underlying mechanisms that result in either the absence of, or diminished or inadequate amounts of insulin and other hormones or which are otherwise produced in aberrant quantities. The combination of therapies provided by the present invention can restore more normal glucose metabolism, including achieving and maintaining appropriate levels of insulin, amylin, postprandial glucose, triglycerides, and glucagon and ameliorate the significant weight gain and increased risk for serious hypoglycemia that is associated with tight glycemic control.

The present invention also provides single agent therapies for treating diabetes and related conditions. These single agent therapies include methods for administering one or more agents that stimulate pancreatic islet cell regeneration and/or transformation of new insulin producing islet cells from pancreatic ductal epithelium to treat diabetes and other diseases and conditions relating to aberrant glucose regulation. In various embodiments, these methods involved the administration of such agents, including but not limited to HIP, hamster INGAP, exendin-4, including synthetic exendin-4, and Liraglutide (NN221), alone or in combination with a dipeptidyl peptidase-4 inhibitors including but not limited Vilidagliptin, Sidagliptin, Saxagliptin and PHX1149. Other agents which also have the potential to expand islet cell mass include gastrin and epidermal growth factor-1 and are included among agents to potentially expand the islet cell mass. Diseases and conditions amenable to treatment with this methodology, include but are not limited to type 1 diabetes, where these treatments can be used to improve glycemic control, as measured by hemoglobin A1C, and to reduce bolus insulin before meals by 10-20%, with reduced fluctuations and decreased postprandial glucose, glucagon, and triglycerides. These methods can also be used to prevent progression of impaired glucose tolerance to diabetes and to prevent progression of impaired fasting glucose to progression to impaired glucose tolerance and diabetes and to reverse newly diagnosed type 2 diabetes. These methods can also be used to treat type 2 diabetes.

Exogenous injectable insulin is a therapy for patients with type 1 diabetes and other conditions in which insulin is either absent or present in diminished or inadequate amounts relative to the glucose content in the bloodstream. Insulin therapy does not treat the underlying mechanisms disease resulting in type 1 diabetes and other such conditions in which there is diminished endogenous insulin production. The therapies, methods, modalities, and treatments described herein are the first to address the many facets of the cause and complications of diabetes. The unique therapies provided by the invention encompass diverse aspects diabetology, metabolism, and immunology. These therapies include those that bring the many different hormones, in addition to insulin, that are diminished or absent in type 1 diabetes. The methods of the invention provide for the regeneration of new insulin producing cells and immuno-modulation that together serve to ameliorate, diminish, or abolish the need for insulin among patients with type 1 diabetes and other conditions associated with inadequate insulin production and secretion.

In type 1 diabetes, there are several underlying mechanisms that result in significant reduction in the production of insulin. These include autoimmune destruction of the islet cell and reduction in regeneration capacity of the ductal epithelium, which may be due to diminished amounts of potent islet cell regeneration hormones. The methods of the present invention are efficacious, because when the autoimmune cells that attack the pancreatic islet cells are blocked, and peptides or other compounds that stimulate regeneration of the pancreatic islet cells are administered, the patient becomes less dependent on insulin administration.

The methods of the invention can even render some patients completely free of their dependence on administered insulin. Other studies (see the references Levetan et al., 2002, *Diabetes* 51(supple 2):429, Levetan et al. *Diabetes* 2002. 51(suppl. 2):474, Levetan *Diabetes* 2001; 50(supple 2):2105 PO. and Levetan et al., 2003, *Diabetes Care* 26:1-8, both incorporated herein by reference) show that, when diminished hormones other than insulin are replaced, insulin requirements in type 1 patients are significantly diminished with improved glucose control. By providing new islet cells and blocking the immune cells that can kill them, the methods of the present invention have even greater promise, because they result in the sustained endogenous production of insulin itself.

There is a demonstrated need for the therapeutic benefits provided by the present invention. There are new insulin formulations and evidence to support that intensive insulin therapy prevents deaths and reduces the rate of blindness, amputations, and kidney failure necessitating dialysis. However, intensive insulin therapy utilizing modern modalities of multiple insulin injections and continuous insulin delivery via pump therapy is associated with a two-to-three fold increased risk of serious hypoglycemia requiring assistance from another person. In a clinical study setting, despite normalization of glucose in type 1 diabetes patients by means of intravenous insulin and glucose, the standard deviation in glucose levels, both high and low, is significantly wider than non-diabetic study subjects with the same average glucose over a 24-hour period.

Thus, despite insulin's availability and new technologies, including new formulations of human insulin, self blood glucose monitoring systems, continuous glucose sensors and pump therapy, normal glucose control is not approximated by current therapies. Moreover, the underlying mechanisms causing type 1 diabetes are not impacted by the current therapies available for patients with type 1 diabetes and conditions in which there is no or diminished insulin production.

The present invention provides new methods and pharmaceutical compositions for treating type 1 diabetes mellitus and other conditions in which the lack of or diminished insulin production is a causative factor for the disease symptoms. The methods and compositions of the invention can reverse the underlying pathologic mechanisms of these disease conditions. Thus, the methods of the invention diminish, and in some cases eliminate, the need for insulin administration to patients formerly in need thereof.

In one embodiment of this method, the agent that stimulates islet cell regeneration and/or transformation from pancreatic duct cells into insulin producing islet cells is selected from the group consisting of Amylin and/or an analog, such as Pramlintide, GIP, GLP-1 and/or homologous compounds and analogs, which include Exendin-4, Liraglutide (NN2211), which are GLP-1 receptor agonists, HIP, HIP analogs, hamster INGAP, INGAP analogs, human INGAP, any biologically active INGAP peptide and the Dipeptidyl Peptidase inhibitors, which delay the degradation of GLP-1. These and other agents useful in this aspect of the invention are described in Section II C, below. Those of skill in the art will appreciate in view of the disclosure herein that more than one agent that stimulates islet cell regeneration and/or ductal cell transformation and/or which slows the degradation of such agents can be used in combination in the methods of the invention.

In the practice of the methods of the invention, the selected agent for increasing islet number, mass, and/or production of endogenously produced insulin is used in combination with a specific agent that inhibits, blocks the activity of, or destroys autoimmune cells that target the pancreatic islet cells. Such agents include, for example, peptides, proteins, and synthetic compounds. In one embodiment, the agent is a monoclonal antibody, a heat-shock protein, DiaPep277 and anti-GAD65 antibody vaccines, the immune agents Mycophenolate mofetil and Daclizumab, the targeted immune agent, Rituximab, an anti CD20 agent, anti CD3 antibody, hOKT3 gamma1 (Ala-Ala) and the monoclonal antibody TRX4 (ChAglyCD3) and other compounds that specifically delay, prevent, or halt autoimmune destruction of the islet cell. These and other agents useful in this aspect of the invention are described in Section II D, below. Those of skill in the art will appreciate in view of the disclosure herein that more than one agent that blocks autoimmune destruction of pancreatic islet cells can be used in combination in the methods of the invention.

Thus, the combination therapies and related methods of the invention involve the co-administration of one or more agents that stimulate islet cell regeneration or ductal cell transformation with one or more agents that block autoimmune destruction of pancreatic islet cells. As used herein, an agent is "co-administered" or "used in combination" with another agent (also referred to herein as, "agent") when the two agents are administered as part of the same course of therapy. In one embodiment, a first agent is first administered prior to administration of the second agent, and treatment with both is continued throughout the course of therapy. In another embodiment, the second agent is administered after the initiation or completion of the therapy involving the first agent. In other embodiments, the first agent is administered contemporaneously with the initiation of the therapy with the second agent. In one embodiment, a therapy involving one or more agents to block or kill autoimmune cells that target pancreatic islet cells is first administered prior to administration of the therapy that stimulates islet cell regeneration or ductal cell transformation or both. In one embodiment, treatment with the specific autoimmune blocker is continued after the cessation of treatment with agents that stimulate islet cell regeneration.

Practice of the methods of the invention can involve multiple rounds, or "cycles," of treatment. Each cycle of one or more administrations of an agent that stimulates islet cell regeneration or ductal cell transformation and one or more administrations of an agent that blocks autoimmune cells that target pancreatic islet cells (as well as a complete set of cycles) can be viewed as practice of the method. Thus, an islet cell regeneration agent can be administered in any or all of the multiple cycles of treatment with the autoimmune cell blocking agent or only in a subset of such cycles, for example. It will be understood that the above examples are for illustration only and not intended to limit the invention in any fashion. Those of skill in the art will also appreciate that in many cases the schedule of co-administration may differ in the first or a later therapeutic cycle for the convenience of the patient.

The combination therapies and related methods of the invention uniquely target the underlying pathologic mechanisms of type 1 diabetes by administering agents that regenerate new islet cells and/or transform pancreatic ductal cells in combination with agents that provide targeted immune therapy. This combination therapy reverses, wholly or partially, the underlying mechanisms of type 1 diabetes, which is an autoimmune phenomena in which anti-self antibodies attack the pancreas. Current therapies for type 1 diabetes that rely on the administration of insulin do not reverse the underlying defects in type 1 diabetes. Moreover, current immune therapies for type 1 diabetes based upon rejection of foreign pancreas cells do not specifically target the immune response causative of the death of the host's pancreas cells.

The new methods provided by the present invention reverse the underlying pathologic mechanisms of diseases and conditions resulting from decreased insulin production due to an imbalance between destruction, regeneration, and sustenance of insulin producing islet cells. The methods and compounds of the invention can reduce the insulin requirements of patients currently taking the drug due to having type 1 diabetes or another disease or condition and can improve glucose control in such patients. In some patients, treatment in accordance with the methods of the invention can ameliorate or obviate the need for administered insulin. The following section describes a variety of diseases and conditions that the methods and compositions of the present invention can be used to treat with therapeutic benefit.

B. Diseases and Conditions Amenable to Treatment

The combination therapies of the present invention can be used to treat any mammal, including humans and animals, suffering from a disease, symptom, or condition related to a diminished production of insulin due to the loss of pancreatic islet cells. Such diseases and conditions include, of course, type 1 diabetes mellitus, pre-diabetes, including but not limited to pre-diabetes in a type 1 patient as manifested by antibodies (anti-GAD65n and others) specific for type 1 diabetes, and latent autoimmune diabetes of adulthood. Moreover, the present invention can be practiced with therapeutic benefit for patients newly diagnosed as having type 1 diabetes, the siblings and first degree relatives of patients with type 1 diabetes, and people with positive antibodies and other autoimmune conditions that indicate a predilection to type 1 diabetes. In one embodiment the methods of the invention are practiced to reverse type 1 diabetes in a patient in need of such treatment.

The combination therapies and related methods and compositions of the invention can also be employed as adjunctive therapy to insulin therapy in type 1 diabetes in children and adults, to ameliorate glucose swings among patients with diabetes, and in patients with poorly controlled diabetes, hypoglycemic unawareness, and recurrent hypoglycemia in type 1 diabetes.

The single agent therapies and related methods and compositions of the invention can be used to treat patients having newly diagnosed type 2 diabetes, type 2 diabetes in children and adults with recurrent hypoglycemia, type 2 diabetes being concurrently treated with insulin therapy, and poorly controlled type 2 diabetes. In some patients, both children and adults, the methods and compositions of the invention can reverse type 2 diabetes. The methods and compositions of the invention can also be used to treat both children and adults having atypical forms of diabetes and patients having the conditions of postprandial hyperglycemia.

The single agent therapies and related methods and compositions of the invention can also be used to treat patients who are children as well as adult patients in need of weight loss, including but not limited to achieve weight loss or treat obesity in patients having type 1 diabetes as well as those who do not have type 1 or 2 diabetes. In one embodiment, the methods and compositions of the invention are used to treat a patient having morbid obesity. In other embodiments, the methods and compositions of the invention are used to treat a patient having morbid obesity or patients having anorexia, bulimia, or other eating disorders.

The single agent therapies and related methods and compositions of the invention can also be used to children and adults having dysmetabolic syndrome or metabolic syndrome, as well as patients exhibiting the conditions of hypertriglyceridemia with and without diabetes and postprandial hypertriglyceridemia. In one embodiment, these methods are practiced to treat polycystic ovarian syndrome in a patient in need of such treatment.

Other patients that can benefit from the single agent therapies and related methods of the invention include children and adult patients diagnosed as having conditions such as fasting hyperglycemia, impaired fasting glucose, impaired glucose tolerance, and hypoglycemic conditions generally.

The single agent therapies and related methods and compositions of the invention can also be used to treat patients having neuropathic pain syndromes and neuropathy, regardless of whether the patient is diagnosed as diabetic.

The single agent therapies and related methods and compositions of the invention can also be used to treat patients having recurrent pancreatitis or pancreatic cancer and can be used in all modalities of auto islet regeneration.

The following sections describe the agents useful in the methods of the invention. Those of skill in the art will appreciate, in view of the disclosure herein, that the skilled artisan may select particular agents based on the disease and condition being treated and the health and medical status of the patient.

C. Agents for Stimulating Pancreatic Islet Cell Regeneration

In one embodiment of the methods of the invention, the agent that stimulates islet cell regeneration and/or transformation from pancreatic duct cells into insulin producing islet cells is selected from the group consisting of amylin and/or an analog, including but not limited to Symlin, Pramlintide, exendin-4, GIP, GLP-1, INGAP, Liraglutide (NN2211), other incretin-mimetic hormones, and/or similarly acting compounds and agents, and agents that extend the half-life or increase the level or activity of any of the foregoing compounds and agents, such as, for example, dipeptidyl peptidase inhibitors, which delay the degradation of GLP-1. There are numerous GLP-1 mimetics that act via direct agonist activity on the GLP-1 receptors or by inhibiting the degradation of GLP-1. These agents are useful in the methods of the invention. GLP-1 mimetics can be used in conjunction with targeted immune therapy for the treatment of type 1 diabetes, and, as provided by the present invention, they can be used to improve glycemic control, as measured by hemoglobin A1C, in type 1 diabetes; to prevent progression of impaired glucose tolerance in diabetes; to prevent progression of impaired fasting glucose to impaired glucose tolerance and diabetes; to reverse newly diagnosed type 2 diabetes; to treat type 2 diabetes, and to treat or prevent obesity, polycystic ovarian syndrome, and neuropathyic pain syndromes.

Methods, agents, and pharmaceutical formulations useful in the practice of the present invention to achieve pancreatic islet cell regeneration include those described in the following references, each of which is incorporated herein by reference: Rosenberg et al., 1992, *Adv. Exp. Med. Biol.* 321: 95-104; March 1996, *Diabetologia* 39(3):256-62; July 1996, *Pancreas* 13(1):38-46; and November 2004, *Ann. Surg.* 240 (5):875-84; Vinik et al., June 1997, *Horm. Metab. Res.* 29(6): 278-93;

In one embodiment of the invention, amylin or an analog is employed in the method to stimulate pancreatic islet cell regeneration. Amylin can be formulated and administered for purposes of the present invention in accordance with the teachings of the reference Young et al., 1997, *Curr. Opin. Endocrin. Diabetes* 4: 282-290, incorporated herein by reference. In one embodiment of the invention, amylin and/or an analog, including but not limited to Pramlintide, is administered subcutaneously and used alone or in conjunction with other islet stimulating peptides. In one embodiment, amylin or Pramlintide is dosed at 0.3-0.8 micrograms per kilogram patient weight. In one embodiment, this dose is administered subcutaneously before meals, for example, QHS and 3 AM. In one embodiment, the therapeutically effective dose is delivered via an infusion device and/or a transdermal, intranasal, buccal, microneedle delivery system to provide a 30-minute continuous infusion time administered, for example, beginning 3-5 minutes before meals, before bedtime, and beginning at about 3 AM. In another embodiment, the therapeutically effective dose is administered utilizing sustained release formulations requiring administration by injection or other delivery method no more frequently than once a week, once every 2 weeks, or once monthly. In some embodiments, amylin or Pramlintide is co-administered with another islet stimulating agent.

In one embodiment of the invention, exendin-4 or an analog is employed in the method to stimulate pancreatic islet cell regeneration. Exendin-4 can be formulated and administered for purposes of the present invention in accordance with the teachings of the following references, each of which is incorporated herein by reference: Alcantara et al., 1998, *Cell Biochem. Funct.* 16(1): 51-6; Dupre et al., 2004, *J. Clin. Endocrin. Metab.* 89(7): 3469-73; Edwards et al., 1999, *Diabetes* 48: 86-93; and Xu et al., 1999, *Diabetes* 48: 2270-76. In one embodiment, exendin-4 is dosed in the range of 0.05-0.50 micrograms per kilogram body weight administered before meals, QHS and 3 AM. In one embodiment, exendin-4 is administered subcutaneously as the islet neogenesis agent alone or in conjunction with other islet stimulating peptides. In one embodiment, the therapeutically effective dose is administered subcutaneously. In one embodiment, the therapeutically effective dose is administered by an infusion device to provide a 30-minute continuous infusion time beginning 3-5 minutes before meals, before bedtime, and beginning at 3 AM. In another embodiment, delivery of exendin-4 is via transdermal, buccal, intranasal or microneedle delivery systems. In another embodiment, the therapeutically effective dose is contained in a sustained release formulation that requires administration no more frequently than once a week, once every 2 weeks, or once monthly. In one embodiment, exendin-4 is co-administered with another islet cell neogenesis or ductal cell transformation agent.

In the single agent therapies of the invention, exendin-4 or synthetic exendin-4 is administered at a dose ranging from 5 to 20 micrograms before meals. This dose will provide patients the ability to reduce bolus insulin before meals by 10-20% with reduced fluctuations and decreased postprandial glucose, glucagon, and triglycerides. Administration of exendin-4 in accordance with the methods of the invention can be used to improve glycemic control, as measured by hemoglobin A1C, in type 1 diabetes; to prevent progression of impaired glucose tolerance in diabetes; to prevent progression of impaired fasting glucose to impaired glucose tolerance and diabetes; to reverse newly diagnosed type 2 diabetes; and to treat type 2 diabetes.

In an embodiment of the combination therapy of the invention, exendin-4 or synthetic exendin-4 is administered of 5 to 25 micrograms, for example 11 micrograms, to an adult patient in the morning, before food intake, and at bedtime for three consecutive weeks. For patients initiating treatment with C-peptide levels lower than about 1.0 ng/mL, C-peptide levels are monitored, and when they rise above 0.5 ng/mL, the Bluestone antibody hOKT3g1 (ala-ala) is administered for 12 consecutive days. In another embodiment, Diapep 77 or a similar agent is used in the combination therapy instead of the Bluestone antibody.

GIP and GLP-1 belong to the incretin family of growth hormones (see the references Creutzfeldt, 1979, *Diabetologia* 16: 75-85; Creutzfeldt and Ebert, 1985, *Diabetologia* 28: 565-573; Holst et al., 2001, *Scand. J. Clin. Lab. Invest. Suppl.* 234: 75-85; and Vilsboll et al., June 2003, *J. Clin. Endocrin. Metab.* 88(6):2706-13, each of which is incorporated herein by reference), and in one embodiment of the invention, an incretin hormone or analog is employed in the method to stimulate pancreatic islet cell regeneration.

In one embodiment of the invention, GIP or an analog is employed in the method to stimulate pancreatic islet cell regeneration. GIP can be formulated and administered for purposes of the present invention in accordance with the teachings of the following references, each of which is incorporated herein by reference: Andersen et al., 1978, *J. Clin. Invest.* 62: 152-161; Creutzfeldt et al., February 1980, *Diabetes* 29(2):140-5; Dupré et al., 1973, *J. Clin. Endocrin. Metab.* 37: 826-828; Ebert et al., 1980, *Clinical Gastroenterology* 9(3): 679-98; Elahi et al., 1979, *Am. J. Physiol.* 237: E185-E191, and 1994, *Regulatory Peptide* 51(1): 63-74; Krarup et al., June 1983, *J. Clin. Endocrin. Metab.* 56(6): 1306-12; Krarup et al., 1987, *Metabolism* 36(7): 677-82; Krarup et al., 1988, *Acta Med. Scand.* 223(5):437-41; Lynn et al., 2003, *FASEB* 17:19-93; Meir et al., 2002, *Regulatory Peptides* 107:1-3; and Nauk et al., 1993, *J. Clin. Endocrin. Metab.* 76(4): 912-7.

In one embodiment, GIP is administered intravenously or subcutaneously alone or in combination with another islet stimulating peptide or agent and dosed at 2-10 nanograms per kilogram patient weight to provide a 30-minute continuous infusion time beginning 3-5 minutes before meals, before bedtime, and beginning at 3 AM. In one embodiment GIP is administered subcutaneously before meals, QHS, and 3 AM. In one embodiment, GIP is administered using an infusion device or a transdermal, buccal, intranasal or microneedle delivery systems. In another embodiment, a sustained release formulation requiring administration no more frequently than once every week, once every 2 weeks, or once monthly injections is employed. Suitable compositions for administering GIP in accordance with the methods of the invention are described in the reference Jones et al., 6 Nov. 1989, *Diabetes Res. Clin. Pract.* 7(4):263-9.

In one embodiment of the invention, GLP-1 or an analog is employed, alone or in combination with an inhibitor of its degradation, such as a DPP inhibitor, in the method to stimulate pancreatic islet cell regeneration. GLP-1 can be formulated and administered for purposes of the present invention in accordance with the teachings of the following references, each of which is incorporated herein by reference: Elahi et al., 1994, *Regulatory Peptides* 51(1): 63-74; Gutniak et al., 1994, *Diabetes Care* 17:1039-44; Kreymann et al., 1987, *Lancet* 2: 1300-1304; Larsen et al., 1996, *Diabetes* 45(Suppl. 2):233A (Abstract); Larsen et al., 2001, *Diabetes Care* 24(8): 1416-21; List et al., 2004, *Am. J. Physiol. Endocrin. Metab.* 286(6): E875-81; Lugari et al., 2000, *Horm. Metab. Res.* 32: 424-428; Marquez et al., March 1998, *Cell. Biochem. Funct.* 16(1):51-6; Meier et al., March 2004, *Critical Care Medicine* 32(3): 848-851; Meneilly et al., 2003, *Diabetes Care* 26: 2835-41; Nauk et al., 1996, *Diabetologia* 39(12):1546-53; Thorens et al., December 1995, *Diabetes Metab.* 21(5):311-8; Vilsboll et al., 2003, *J. Clin. Endocrin. Metab.* 88(6): 2706-13; Wang et al., 1997, *J. Clin. Invest.* 99: 2883-2889; and Zander et al., 2002, *Lancet* 359: 824-30.

In one embodiment, GLP-1 is administered subcutaneously alone or in combination with other islet stimulating peptide or compound and dosed at 0.5-2.0 micrograms per kilogram patient weight. In one embodiment GLP-1 is administered subcutaneously before meals, QHS, and 3 AM. In one embodiment, GLP-1 is administered using a continuous subcutaneous infusion device at a rate of 1-30 ng/kilogram body weight/minute or a transdermal, buccal, or microneedle delivery system to provide a 30-minute continuous infusion time beginning 3-5 minutes before meals, before bedtime, and beginning at 3 AM. In another embodiment, a sustained release formulation requiring administration no more frequently than once every week, once every 2 weeks, or once monthly injections is employed.

In one embodiment, HIP is administered either orally or subcutaneously at a dosage of 800 mg/day or hamster INGAP is administered subcutaneously alone or in combination with another islet stimulating peptide or compound and dosed at 5.0-15.0 milligrams per kilogram patient weight per body weight per day. In one embodiment INGAP is administered in a continuous subcutaneous infusion over 24 hours. In one embodiment, INGAP is administered in divided dosages pr day before meals, QHS, and 3 AM. In one embodiment, INGAP is administered using a continuous infusion device, transdermal patch, microneedle delivery system to provide a consistent basal level delivery of INGAP. In another embodiment, INGAP is delivered in a continuous infusion with bolus delivery before meals. In another embodiment, a sustained release formulation requiring administration no more frequently than once every week, once every 2 weeks, or once monthly injections is employed.

In one embodiment, Liraglutide (NN2211) is administered subcutaneously alone or in combination with another islet stimulating peptide or compound in dosages of 10-40 micrograms per kilogram body weight. In one embodiment Liraglutide is administered subcutaneously before meals, QHS, and 3 AM. In one embodiment, Liraglutide is administered using an infusion device or a transdermal, buccal, or microneedle delivery system to provide a 30-minute continuous infusion time beginning 3-5 minutes before meals, before bedtime, and beginning at 3 AM. In another embodiment, a sustained release formulation requiring administration no more frequently than once every week, once every 2 weeks, or once monthly injections is employed.

In the single agent therapies of the invention, Liraglutide or NN2211 is administered at a dose of about 20 micrograms per kg of patient weight daily. This dose will provide patients the ability to reduce bolus insulin before meals by 10-20% with reduced fluctuations and decreased postprandial glucose, glucagon, and triglycerides. Administration of Liraglutide in accordance with the methods of the invention can be used to improve glycemic control, as measured by hemoglobin A1C, in type 1 diabetes; to prevent progression of impaired glucose tolerance in diabetes; to prevent progression of impaired fasting glucose to impaired glucose tolerance and diabetes; to reverse newly diagnosed type 2 diabetes; and to treat type 2 diabetes.

In an embodiment of the combination therapy of the invention, Liraglutide or NN2211 is administered at a dose of about 20 micrograms per kg of patient weight to an adult patient in the morning, about 4 hours before food intake, and at bedtime for three consecutive weeks. For patients initiating treatment with C-peptide levels lower than about 1.0 ng/mL, C-peptide levels are monitored, and when they rise above 0.5 ng/mL, the antibody hOKT3g1 (ala-ala) is administered for 12 consecutive days.

D. Agents that Inhibit, Block, or Destroy the Autoimmune Cells that Target Pancreatic Islet Cells Autoimmune cells that target pancreatic islet cells, especially the insulin-producing beta cells, play a causative role in the diseases and conditions treatable in accordance with the methods of the invention. See the references Bach et al., 2001, *Ann. Rev. Immun.* 19: 131-161; Lernmark et al., *Endocrin. Metab. Clin. N. Am.* 20(3): 589-617; and Mathis et al., December 2001, *Nature* 414(6865): 792-798, each of which is incorporated herein by reference. Prior methods of treatment involving the introduction of new pancreatic islets to replace those lost to autoimmune cell attack, employed at most only generalized immune therapy to suppress the rejection of the newly introduced cells.

As opposed to the generalized immune therapy used to prevent rejection in a host, such as a patient receiving transplanted pancreatic cells from a donor, the methods of the invention provide specific maintenance of self-generated new pancreatic islet cells within the individual. Thus, the methods of the invention do not employ agents that provide generalized immune therapy. Generalized immune therapies include the current state-of-the-art islet cell (Edmonton Protocol) and the current modern whole pancreas transplantation techniques, which utilize general anti-rejection drugs such as Sirolimus (Rapamycin) and Tacrolimus (FK506).

Instead, the methods of the present invention employ agents that specifically inhibit the activity of or block or destroy the autoimmune cells that target pancreatic islet cells that produce insulin, amylin, or glucagon. Such agents include immunomodulatory peptides that arrest pancreatic islet cell destruction. For example, one such agent is a monoclonal antibody that can delay the progression of islet cell loss or slow or stop the onset of type 1 diabetes. Anti-CD3 antibodies constitute a general class of agents useful in the methods of the invention. For example, suitable anti-CD3 antibodies for purposes of the present invention include the TRX4 antibody under development by TolerRx and the Bluestone humanized anti-CD3 antibody described in the reference Herold et al., 30 May 2002, *NEJM* 346(22): 1692-1698, incorporated herein by reference. In one embodiment, the Bluestone humanized anti-CD3 antibody is delivered intravenously, 14 days per year in the dosage of 1-1.42 µg/kg on day 1, 5.67 µg/kg on day 2, 11.3 µg/kg on day 3, 22.6 µg/kg on day 4 and 45.4 µg/kg on days 5-14.

In another embodiment, the immuno-modulatory compound is a heat shock protein that can arrest or slow islet cell destruction. Such proteins include DiaPep277, a heat-shock protein under development by Develogen AG (see the reference Raz et al., 2002, *Lancet* 358(9295):1749-53, incorporated herein by reference). In one embodiment, Diapep277 is delivered subcutaneously by giving 1 mg in 40 mg mannitol in vegetable oil subcutaneously at baseline and at one month and then at 3 month intervals. In one embodiment of the combination therapy of the invention, INGAP is co-administered with DiaPep277 as follows. The DiaPep277 is first administered subcutaneously at a dose of about 1 mg, about 30 days prior to the initiation of the INGAP therapy. A second administration of the DiaPep277 is then made at the time (30 days after the first administration) of initiating the INGAP therapy. The INGAP is delivered by 24 hour continuous subcutaneous infusion at a dose of about 8 to 18 mg per kg of patient body weight per 24 hours. The INGAP therapy is continued for an extended period of time, from several months to years, and the DiaPep277 is administered intermittently during the INGAP therapy, at a frequency of about every 3 months.

The immuno-modulatory agents useful in the methods of the invention can be formulated, administered, and dosed as known in the art or as described herein. The following section describes pharmaceutical formulations and dosing and administration protocols for practice of the methods of the invention.

III. Pharmaceutical Compositions, Dosing and Administration

Dosing and administration of the agents useful in the methods of the invention as described herein provide accelerated islet cell regeneration and/or transformation of ductal cells to optimize an individual's ability to secrete insulin from endogenous, newly formed islet cells as well as the lowest toxicity for the agents that delay or prevent the destruction of pancreatic islet cells. Pharmaceutical compositions of the invention provide for kinetic delivery of these agents, ease of delivery, and enhanced efficacy.

The agents useful in the methods of the invention can be administered by a variety of routes. Known agents useful in the methods of the invention can be administered by routes and using pharmaceutical formulations previously developed for other indications. Such delivery routes include, at least for most known agents, oral delivery, topical delivery, including micelle and nanosphere topical delivery systems, subcutaneous delivery including pump-assisted continuous infusion and disposable micro-pumps and micro-needles (including but not limited to those available from Animas Corp.), and buccal delivery.

Of course, the particular route of administration and pharmaceutical formulation of an agent used in the practice of the methods of the invention will be selected by the practitioner based on a patient's disease or condition being treated and the agent employed. A wide variety of pharmaceutical compositions can be employed in the methods of the invention. In some embodiments, extended use preparations can be used for ease of administration and increased efficacy. In one embodiment, one or more of the agents employed in the method is formulated as a micelle.

Often, ease of administration is best achieved by oral delivery. While small molecule pharmaceutical agents can often be readily formulated for oral delivery, peptide and protein-based pharmaceutical agents can be more difficult to formulate for oral delivery. However, suitable formulation technology exists, and in one important aspect, the present invention provides pharmaceutical compositions of proteins and peptides formulated for oral delivery. In one embodiment, the pharmaceutical compositions useful in the methods of the invention suitable for oral delivery are formulated generally in accordance with known Technosphere™ technology developed by MannKind Corp., Eligen® Technology developed by Emisphere, and nasal delivery systems developed by Nastech.

Agents that can be formulated for oral delivery and employed in the methods of the invention include Amylin, Exendin-4, INGAP, INGAP analogs, biologically active hamster INGAP or the biologically active human INGAP, GIP, GLP-1, Liraglutide (NN2211), Pramlintide, analogs and peptide and proteins or non-peptidic mimetics with similar action or homology to the preceding agents, monoclonal antibodies designed to delay the progression of islet cell loss or prevent the onset of type 1 diabetes in both children and adults, including anti-CD3 antibodies, and particularly including the TRX4 antibody under development by TolerRx and the Bluestone anti-CD3 antibody described in the reference Herold et al., supra, as well as other agents that delay the progression of islet cell loss, which may include, but are not limited to DiaPep277, a heat shock protein, under development by Develogen.

Other oral delivery and encapsulation technology suitable for use in making the pharmaceutical compositions of the invention includes the hepatic delivery vesicle (HDV) and pancreatic delivery vesicle (PDV) technology under development by SDG, Inc. and AMDG, Inc. See the reference Davis et al., 2001, *J Diabetes Comp.* 15(5): 227-33, incorporated herein by reference, for a description of the technology. HDV technology can, as provided by the present invention, can be used to deliver GLP-1 directly to the liver. PDV technology provides liposomes with a conjugated protein or other molecule on its surface that targets an agent, such as a peptide that stimulates islet cell neogenesis, directly to the pancreas.

EXAMPLE

Clinical Trial Protocol

In one embodiment of the invention, called a Pancreatic Restorative Therapy (PRT™) method, an agent that stimulates neogenesis of alpha, beta and delta cells of the pancreas in Type 1 and 2 diabetics, Islet Neogenesis Associated Peptide (INGAP), which in type 1 patients is administered in combination with a DiaPep277, a protein that has been utilized specifically to prevent autoimmune islet cell destruction in man.

The therapeutic aim of the treatment is to achieve pancreatic islet cell replacement by the stimulation of new islet cell formation and replication in the patient's own pancreas by reactivating islet neogenesis and islet proliferation with a unique methodology of islet maintenance once new islets have been generated. The results sought include the establishment of normal glucose homeostasis throughout the body by having it make and secrete normal levels of insulin, amylin and glucagon.

This embodiment of the invention is expected to offer substantial advantages over current treatments for both type 1 and type 2 diabetes and reduce the complications of hypoglycemia and hyperglycemia, and/or the need for insulin injections.

Human clinical data has shown a statistical increase in the levels of C-peptide among type 1 diabetes patients in trials utilizing one subcutaneous INGAP injection per day with similar potential benefits including improved cholesterol metabolism demonstrated in type 2 patients.

This embodiment of the combination therapies of the present invention combines this most promising islet regenerating peptide with the best immune modulator that has been designed specifically to prevent destruction of new pancreas cells, DiaPep277.

The usage of both an islet regenerator coupled with a targeted immune blocker to inhibit the destruction of new islets has benefits that could far surpass either therapy alone in that it may take a great deal of time to regenerate islets in the face of ongoing islet destruction. Immune therapy alone may not be successful in regenerating islets in a patient with type 1 diabetes for many years, even in the face of blocking the autoimmune destruction.

The potential for enhanced success over the use of either therapy alone has unique benefits for the patient with type 1 diabetes. The plasticity of the beta cells in type 1 diabetes has been demonstrated in several settings, including pregnancy and among those undergoing renal transplant in which there is evidence to support the new generation of c-peptide decades after the onset of diabetes.

To date, while trials are being conducted with compounds such as exendin-4, Liraglutide (NN2211), GLP-1, which may enhance regeneration from existing islet cells and play a role in reducing apoptosis, but have not been shown to transform pancreatic ductal cells into new alpha, beta and delta cells, there have been no trials with INGAP for such purposes. Thus, the single agent administration of INGAP in patients with type 1 and 2 diabetes in and of itself, offers a unique advantage to other therapies on the market.

The only immune blockers that are being used in clinical trials in type 1 patients, including the Edmonton Protocol for islet transplantation and the NIH's trial with exendin-4 in type 1 patients, are utilizing sirolimus (Rapamycin) and tacrolimus (FK5060 as their immune suppressant agents. Both of these agents are nonspecific agents which are currently being used in pancreas, heart, liver and kidney transplants to prevent rejection of foreign organs and cells. Given that INGAP has the potential to restore an individual's own islets, the need for general immune suppressants like siroliumus (Rapamycin) and tacrolimus (FK506), which are particularly toxic to the kidneys of patients with type 1 diabetes, are not needed; rather, as provided in the combination therapies of the invention, a specific blocker of the CD3 antibodies which attack the pancreas is more efficacious and less toxic.

One specific immune modulatory peptide is DiaPep277. The 60 kDa heat-shock protein (hsp60) is one of the known target self antigens. DiaPep277 is a immunomodulatory peptide from hsp60, p277 which has demonstrated the ability to arrest beta-cell destruction and maintained insulin production in type 1 diabetes patients with a significantly lower need for exogenous insulin in randomized prospective trials. Additionally, among those who received DiaPep277, there was an enhanced shift from T-helper-1 to T-helper 2 cytokines produced by the T lymphocytes.

Although trials with INGAP (without an immune suppressant drug) dosed at 300 mg or 600 mg once subcutaneously did not show reduction in fasting glucose or A1C, they did demonstrate a significant increase in arginine stimulated c-peptide in type 1 and 2 patients. The protocol described herein takes into account many issues that were not addressed in the prior trials, including that the dose of INGAP was not based upon mg/kg/body weight and was given only once per day and no immune suppressant was given during the previous trials.

A critical step to restoration of islet function is aggressive and tight glucose control eliminating glucose fluctuations prior to initiation of therapy, because hormones like GLP-1, GIP, and amylin are blocked in the face of hypoglycemia and hyperglycemia resulting in significant pancreatic glucose toxicity.

The methods of the present invention are effective in the treatment Type 1 and Type 2 diabetes. The methods are effective in type 1 patients when Diapep277 is utilized in conjunction with INGAP. There will be earlier effects in patients with type 1 diabetes who still are able to produce c-peptide on arginine stimulation. The methods are effective in type 2 patients, both those on insulin and those on medications and, in some embodiments, will allow for diminished need for and/or discontinuation of existing diabetes therapies.

The first trial takes into consideration that long standing type 1 and type 2 patients may have a substantially reduced beta cell mass and baseline arginine stimulated c-peptide, as well as meal stimulated values, and so can best evaluate the success of this new therapy and serve as efficacy endpoints.

The first trial is in type 1 and 2 diabetic patients. The initial trial is a 10 month trial including a 6-month intervention preceded by a 4-month intensive glucose management program. In type 1 patients, there will be baseline subcutaneous injections of DiaPep277 which will be followed by subcutaneous injection every three months. Once islet cells have been regenerated and insulin independence is achieved, the need for ongoing INGAP may diminish with only the need for the Diapep277 injection on a 3 month basis. Type 2 patients may also see similar benefits with INGAP alone, and insulin independence, will also reduce the anabolic effects of exogenous insulin including weight gain.

The proposed initial trial is followed by a pivotal trial that can lead directly to FDA approval. In the larger pivotal trial, the duration of dosing and the interval between treatment cycles is investigated, as well as efficacy in more diverse populations including first degree relatives of patients with type 1 diabetes who are GAD65 antibody positive, newly diagnosed type 1 and 2 diabetes, prediabetes, the metabolic syndrome, polycystic ovarian syndrome and in patients with secondary causes of diabetes such as pancreatitis or medication induced, such as steroid and pentamindine therapy.

The initial trial will measure the efficacy of INGAP (Islet Neogenesis Associated Peptide) alone and in combination with Diapep277 (a head shock protein) on carbohydrate metabolism and C-peptide production in patients with type 1 and 2 diabetes; the ability of INGAP and DiaPep277 alone and in combination to initiate beta cell function as measured by C-peptide in patients with type 1 diabetes who have detectable, significantly reduced, or undetectable baseline levels of C-peptide; the effects of INGAP delivered in a continuous subcutaneous infusion on islet cell regeneration and transformation as measured by C-peptide; and the impact of DiaPep277 in islet regeneration and transformation on beta cell function.

Type 1 diabetes is an autoimmune disease afflicting millions of people in the United States. Type 1 diabetes is characterized by the immune system attacking the cells of the pancreas that make and regulate a number of vital hormones that regulate the body's usage of glucose including insulin, glucagon, amylin, Glucagon-Like Peptide-1 (GLP-1), and Glucose-Dependent Insulinotropic Polypeptide (GIP). These hormones and others also regulate and activate the process by which cells of the pancreas are normally regenerated throughout an individual's lifetime. This trial will examine the effects of INGAP and DiaPep 277 given individually as well as in combination in the regeneration, transformation and sustenance of new pancreatic cells.

Patients between 6 and 60 years of age who have type 1 and 2 diabetes mellitus are eligible for this 10-month study. They must have had diabetes for at least 3 years and require insulin treatment. Potential participants will be screened with a questionnaire, followed by medical history and physical examination, blood tests, skin test for tuberculosis and arginine stimulated C-peptide test.

Participants and their families must be willing to undergo a an intensive diabetes self-management and education program with the goal of achieving optimal glycemic control prior to trial entry and be committed to frequent blood glucose monitoring and understand the risks of intensive insulin therapy including hypoglycemia. Patients must be willing to administer insulin via an insulin pump (preferred) or take at least four injections per day. All participants must be willing to learn how to use and be willing to utilize continuous subcutaneous pump therapy for administration of medications throughout the study period.

Patients accepted will participate in a 4-month run-in phase which will encompass intensive glucose optimization. During this time period, all patients will learn how to perform intensive management which may utilize continuous subcutaneous medication delivery. Throughout the duration of the trial, patients will continue to use insulin as required and will maintain diaries recording blood glucose levels and insulin use. Based upon glucose values, insulin dosages will be adjusted according throughout the trial to maintain tight glycemic control with a minimum of hypo or hyperglycemic excursions.

Study participants will undergo arginine-stimulated C-peptide test at the time of entry and at the end of the 3-month glucose optimization period. This will measure the body's insulin production. The patient is injected with a liquid containing arginine, a normal constituent of food that increases insulin release from beta cells into the blood stream. After the injection, seven blood samples are collected over 10 minutes.

Study participants will undergo a mixed meal stimulated C-peptide test with acetaminophen at entry and following the 4-month glucose optimization period. This test assesses the response of the beta cells to an ordinary meal and the time it takes for food to pass through the stomach. The patient drinks a food supplement and takes acetaminophen. Blood samples are then drawn every 30 minutes for 4 hours to measure levels of various hormones and the concentration of acetaminophen.

Immediately following the 3-month optimization period, all patients will undergo a euglycemic clamp study to evaluate the body's sensitivity to insulin. The patient will be admitted to a clinical research facility the evening before the trial and receive an insulin drip through an intravenous line overnight to maintain normal blood sugar levels. The next morning, another intravenous line is placed, while glucose and insulin are being infused and frequent blood samples are being collected to measure blood sugar and insulin levels.

At the 6-month intervention period, the type 1 patients are randomly assigned to receive either (1) INGAP alone delivered by continuous subcutaneous infusion with delivery of 5-15 mg/kg/body weight per day; for example a 70 kg man may received 800 mg (~10 mg/kg over 24 hours); or (2) DiaPep277 alone; or (3) INGAP delivered in a continuous subcutaneous infusion along with interval injections of DiaPep277; or (4) a placebo with no therapy; and the type 2 patients treated on insulin will receive subcutaneous INGAP only during the test period.

During the first 4 months, all patients who are enrolled will be expected to optimize their glycemic control. The use of insulin pumps, glucose sensors, and/or intensive self-blood glucose monitoring may be among the strategies employed.

Type 1 patients will be enrolled into one of 4 treatment arms described above. In one treatment arm, INGAP is delivered by a 24 hour continuous subcutaneous infusion in a dosage of 8-18 mg/kilogram body weight/24 hour time period delivered in conjunction with Diapep277.

The arm of patients receiving both compounds will receive DiaPep277 delivered one month prior to the initiation of a continuous administration of the INGAP. The DiaPep277 will be delivered subcutaneously in a dosage of 1 mg. The DiaPep277 will again be administered subcutaneously 30 days after the initial dosage, at which time, a continuous administration of INGAP will be initiated and continued. The DiaPep277 will be administered throughout the course of the continuous administration of INGAP every 3 months.

In one treatment arm, type 1 patients will receive Diapap277 at the end of the four month intensification of glucose period. The DiaPep277 will be administered in one 1 mg subcutaneous injection and again in 4 weeks, followed by injection every 3 months. In one treatment arm, type 1 patients will receive only INGAP administered in a continuous subcutaneous infusion for 6 months. In one treatment arm, type 1 patients will be followed without active drug for 6 months. In one treatment arm, type 2 patients will receive continuous infusion of INGAP based on their weight and delivered fro 6 months.

All patients have three arginine-stimulated C-peptide tests at the end of each 4 week period of the 10-month study period in addition to a euglycemic clamp study and mixed meal study at the end of the 10-month test period. Drug side effects, laboratory studies will be extensively monitored throughout the study. Treatment and evaluation may be extended beyond the 10-month study period for patients who benefit from the treatment.

For this trial, type 1 diabetes mellitus will be defined by the following: insulin dependence; current or past anti-islet antibodies (anti-insulin before initiation of insulin therapy, anti-islet cell (ICA), anti-tyrosine phosphatase IA-2, and/or anti-glutamic acid decarboxylase (GAD65) antibodies); and a BMI greater than or equal to 20 kg/meter squared and less than or equal to 30 kg/meter squared. For this trial, type 2 diabetes will be defined by the following: insulin-requiring diabetes; absence of and no prior history of anti-islet antibodies (anti-insulin before initiation of insulin therapy, anti-islet cell (ICA), anti-tyrosine phosphatase IA-2, and/or anti-glutamic acid decarboxylase (GAD65) antibodies); and a BMI greater than or equal to 20 kg/meter squared and less than or equal to 30 kg/meter squared.

Exclusion criteria include symptomatic gastroparesis; diabetic nephropathy with a creatinine clearance less than 60 cc/min or 24-hour urine albumin greater than 300 mg; insulin requirements greater than 0.8 units/kg/day; hypoglycemia unawareness (unless easily corrected via simple modifications in the patient's diabetes regimen, the potential enrollee will be excluded if he/she has suffered greater than or equal to 2 episodes of severe hypoglycemia during the most recent 12 months, defined as requiring assistance from a third party, receiving assistance from medics, visiting an ER or being hospitalized due to the hypoglycemia); hyperlipidemia, whether untreated or resistant to medical treatment, with LDL cholesterol greater than 110 mg/dL or TG greater than 300 mg/dL; evidence of chronic infection; history of any malignancy; any chronic medical condition that unduly increases risk for the potential enrollee as judged by study investigators; hematologic abnormalities, including anemia (hematocrit less than 31.8% in women and less than 36.7% in men); leukopenia (WBC count less than 3.4 K/mm(3)); thrombocytopenia (platelet count less than 162 K/mm(3)); hypertension, whether untreated or resistant to medical treatment, with blood pressure greater than 140/85 mm Hg; and pregnancy, breastfeeding or planned pregnancy within two years.

The safety endpoints will include incidence of adverse events (AEs) and serious adverse events (SAEs) during the study period; clinical assessment of laboratory variables; and vital signs. The efficacy endpoints will include blood glucose levels; glucose tolerance test; insulin dosage; C-peptide levels, basal and stimulated; hemoglobin A1C levels; occurrence of hypoglycemic episodes; and patient diaries.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for treating type 1 diabetes mellitus or a disease or condition resulting from the loss of pancreatic islet structures in a patient, said method comprising administering to said patient (i) an agent that stimulates pancreatic islet cell regeneration selected from a peptide consisting of HIP 1 (SEQ ID NO: 6), a peptide consisting of HIP 2 (SEQ ID NO: 1) and a combination thereof; and (ii) an agent that specifically inhibits the activity of autoimmune cells in said patient that target and destroy pancreatic islet structures selected from a monoclonal antibody, a heat shock protein an immunomodulatory compound and a combination thereof.

2. The method of claim 1, wherein the patient achieves restoration of normal glucose metabolism.

3. The method of claim 1, wherein the patient achieves restoration of normal hormonal function.

4. The method of claim 1, wherein said agent that specifically inhibits the activity of autoimmune cells in said patient that target and destroy cells of the pancreatic islet structures is an anti-GAD65 antibody.

5. The method of claim 1, wherein beta-cell mass is increased in said patient.

6. The method of claim 1, wherein hyperglycemia is reduced in said patient.

7. The method of claim 1, wherein the agent that stimulates pancreatic islet cell regeneration and the agent that specifically inhibits the activity of autoimmune cells in said patient that target and destroy pancreatic islet structures are administered in parallel.

8. The method of claim 1, wherein the agent that stimulates pancreatic islet cell regeneration and the agent that specifically inhibits the activity of autoimmune cells in said patient that target and destroy pancreatic islet structures are co-administered.

9. The method of claim 1, wherein the agent that stimulates pancreatic islet cell regeneration and the agent that specifically inhibits the activity of autoimmune cells in said patient that target and destroy pancreatic islet structures are administered in a co-formulation.

10. The method of claim 1 further comprising administering a second agent that stimulates pancreatic islet cell regeneration.

11. The method of claim 10, wherein the second agent that stimulates pancreatic islet cell regeneration is selected from amylin, pramlintide, an incretin hormone, gastric inhibitory peptide (GIP), glucagon-like peptide 1 (GLP-1), glucagon-like peptide 1 (GLP-1) mimetics, exendin-4, synthetic exendin-4, liraglutide, a human proislet peptide, hamster INGAP, a dipeptidyl peptidase inhibitor and combinations thereof.

12. The method of claim 1, wherein the agent that specifically inhibits the activity of autoimmune cells in said patient that target and destroy pancreatic islet structures is an anti-CD3 antibody.

* * * * *